United States Patent
Masih et al.

(10) Patent No.: US 10,514,370 B2
(45) Date of Patent: Dec. 24, 2019

(54) METHODS AND SYSTEMS FOR MEASURING ANIONS

(71) Applicant: King Abdullah University of Science and Technology, Thuwal (SA)

(72) Inventors: Dilshad Masih, Thuwal (SA); Omar F. Mohammed, Thuwal (SA); Shawkat M. Aly, Thuwal (SA); Erkki Alarousu, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 131 days.

(21) Appl. No.: 15/041,098

(22) Filed: Feb. 11, 2016

(65) Prior Publication Data

US 2016/0238582 A1 Aug. 18, 2016

Related U.S. Application Data

(60) Provisional application No. 62/115,354, filed on Feb. 12, 2015.

(51) Int. Cl.
*G01N 33/18* (2006.01)
*G01N 21/64* (2006.01)
*G01N 33/84* (2006.01)
*G01N 33/58* (2006.01)

(52) U.S. Cl.
CPC ....... *G01N 33/182* (2013.01); *G01N 21/6428* (2013.01); *G01N 33/582* (2013.01); *G01N 33/84* (2013.01); *G01N 21/6408* (2013.01); *G01N 2021/6432* (2013.01)

(58) Field of Classification Search
CPC ...... G01N 31/22; G01N 33/182; G01N 33/84; G01N 21/6428; G01N 21/6408; G01N 2021/6432
See application file for complete search history.

(56) References Cited

PUBLICATIONS

Borisov, S. M. et al. "New optical sensors for oxygen based on phosphorescent cationic water-soluble Pd(II), Pt(II), and Rh(III) porphyrins." Journal of Analytical Chemistry (2004) 59 155-159.*
Gouterman, Martin. "Optical spectra and electronic structure of porphyrins and related rings" pp. 27-34 from Chapter 1 in "The Porphyrins" vol. III. Edited by David Dolphin. Academic Press 1978.*
Papkovsky, Dmitri et al. "Optical sensing of sulfite with a phosphorescent probe." Analytica Chimica Acta (1998) 374 1-9. (Year: 1998).*
Shangwen, et al., "A mechanosynthesized, sequential, cyclic fluorescent probe for mercury and iodide ions in aqueous solutions", Spectrochimica Acta Part A: Molecular and Biomolecular Spectroscopy, 2014, pp. 223-228.
Aradhana, et al., "Dual colorimetric sensing of mercury and iodide ions by steroidal 1,2,3-triazole-stabilized silver nanoparticles", The Royal Society of Chemistry, 2014, 39866-39869.
Basumatary, et al., "Selective iodide chemosensing through a redox active Cu-corrole", RSC Advances, 2014, 28417-28420.
Bianchi, et al., "Aspects of Anion Coordination from Historical Perspectives", Preface, 2012, 567.
Brown, et al., "Effect of Toxic Doses of A Novel Histamine (H2) Antagonist of the Ray Thyroid Gland", 1987, 787-794.
Carasel, et al., "Halide Ions Complex and Deprotonate Dipicolinamides and Isophthalamides: Assessment by Mass Spectrometry and UV-Visible Spectroscopy", American Chemical Society, 2010, 8112-8116.
Chouhaid, et al., "Role of Iodide in Photoelectrochemical Solar Cells. Electron Transfer between Iodide Ions and Ruthenium Polypyridyl Complex Anchored on Nanocrystalline SiO2 and SnO2 Films", 4944-4951, 1998.
Concepcion, et al., "Photophysics and halide quenching of a cationic metalloporphyrin in water", Photochemical & Photobiological Sciences, 2013, 1079-1085.
Dasary, et al., "A surface enhanced Raman scattering probe for highly selective and ultra sensitive detection of iodide in water and salt samples", The Royal Society of Chemistry, 2013, 1195-1203.
Eastwood, et al., "Porphyrins XVIII. Luminescence of (Co), (Ni), Pd, Pt Complexes", Journal of Molecular Spectroscopy 35, 1970, 359-375.
El-Ballouli, et al., "Quantum Confinement-Tunable Ultrafast Charge Transfer at the PbS Quantum Dot and Phenyl-C61-butyric Acid Methyl Ester Interface", American Chemical Society, 2014, 6952-6959.
El-Ballouli, et al., "Real-Time Observation of Ultrafast Intraband Relaxation and Exciton Multiplication in PbS Quantum Dots", American Chemical Society, 2014, 285-292.
Fang, et al., "A dual model logic gate for mercury and iodide ions sensing based on metal-organic framework MIL-101", RSC Advances, 2014, 37349-37352.
Fangkai, et al., "Carbon dots-based fluorescent probes for sensitive and selective detection of iodide", Springer, 2013, 453-460.

(Continued)

*Primary Examiner* — Christopher Adam Hixson
(74) *Attorney, Agent, or Firm* — Billion & Armitage; Gregory S. Schwartz

(57) ABSTRACT

Embodiments of the present disclosure provide for methods for detecting the presence and/or concentration of anions in a solution, systems for detecting the presence and/or concentration of anions in a solution, anion sensor systems, and the like.

11 Claims, 14 Drawing Sheets

(56) References Cited

PUBLICATIONS

Finikova, et al., "Dynamic quenching of porphyrin triplet states by two-photon absorbing dyes: Towards two-photon-enhanced oxygen nanosensors", Journal of Photochemistry and Photobiology A: Chemistry 198, 2008, 75-84.

Francisco, et al., "Gold nanoelectrode ensembles for direct trace electroanalysis of iodide", Analytica Chimica Acta 575, 2006, 16-24.

Gale, et al., "Anion receptor chemistry: highlights from 2011 and 2012", Royal Society of Chemistry, 2014, 205-241.

Galievsky, et al., "Excited States of Water-Soluble Metal Porphyrins as Microenvironmental Probes for DNA and DNA-Model Compounds: Time-Resolved Transient Absorption and Resonance Raman Studies of Ni(TMpy-P4) in [Poly(dG-dC)]2 and [Poly(dA-dT)]2", J. Phys. Chem., 1996, 12649-12659.

Geddes, et al., "Optical halide sensing using fluorescence quenching: theory, simulations and applications—a review", Institute of Physics Publishing, 2001, 53-88.

Gefei, et al., "Highly sensitive and selective colorimetric detection of iodide based on anti-aggregation of gold nanoparticles", Analytical Methods, 2013, 2188-2192.

Haimin, et al., "Determination of Iodide via Direct Fluorescence Quenching at Nitrogen-Doped Carbon Quantum Dot Fluorophores", American Chemical Society, 2014, 87-91.

Htun, "A Negative Deviation from Stern—Volmer Equation in Fluorescence Quenching", Journal of Fluorescence, vol. 14, No. 2, Mar. 2004, 217-222.

Hussain, et al., "Thiazole-Containing Conjugated Polymer as a Visual and Fluorometric Sensor for Iodide and Mercury", American Chemical Society, 2013, 2234-2240.

Jammoul, et al., "Photoinduced oxidation of sea salt halides by aromatic ketones: a source of halogenated radicals", Atmospheric Chemistry and Physics, 2009, 4229-4237.

Jun, et al., "A reversible and highly selective fluorescent probe for monitoring Hg2+ and iodide in aqueous solution", Sensors and Actuators B, 2014, 613-623.

Keane, et al., "Triplet-state dynamics of a metalloporphyrin photosensitiser (PtTMPyP4) in the presence of halides and purine mononucleotides", Photochemical & Photobiological Sciences, Jun. 2, 2011, 1503-1716.

Kobayashi, et al., "Energy Relaxation Mechanism In Ni(II), Pd(II), Pt(II) and Zn(II) Porphyrins", Photochemistry and Phorobralogy, Sep. 19, 1978, 925-931.

Kruk M.M., et al., "Highly Sensitive Halide Ions Recognition with Diprotonated Porphyrin", Macroheterocycles, 2008, 50-58.

Lang, et al., "Broadband ultraviolet-visible transient absorption spectroscopy in the nanosecond to microsecond time domain with sub-nanosecond time resolution", Review of Scientific Instruments 84, 2013, 1-10.

Ryu, et al., "Visible-Light-Induced Water Splitting Based on Two-Step Photoexcitation between Dye-Sensitized Layered Niobate and Tungsten Oxide Photocatalysts in the Presence of a Triiodide/Iodide Shuttle Redox Mediator", Journal of the American Chemical Society, 2013, 16872-16884.

Lingyun, et al., "Carbazole and triazole-containing conjugated polymer as a visual and fluorometric probe for iodide and mercury", Sensors and Actuators B, 2014, 572-580.

Mani, et al., "Generation of Phosphorescent Triplet States via Photoinduced Electron Transfer: Energy and Electron Transfer Dynamics in Pt Porphyrin-Rhodamine B Dyads", J Phys Chem A. Author manuscript, Apr. 12, 2013, 3598-3610.

Meekins, et al., "Role of Water Oxidation Catalyst IrO2 in Shuttling Photogenerated Holes Across TiO2 Interface", J. Phys. Chem. Lett., 2,, 2011, 2304-2310.

Mehata M.S., et al., "Fluorescence quenching of 6-methoxyquinoline: an indicator for sensing chloride ion in aqueous media", Journal of Luminescence 99, 2002, 47-52.

Mishra, et al., "Determination of iodide by derivatization to 4-iodo-N,N-dimethylaniline and gas chromatography—mass spectrometry", The Royal Society of Chemistry, 2000, 459-464.

Miura, et al., "Rapid ion chromatography of L-ascorbic acid, nitrite, sulfite, oxalate, iodide and thiosulfate by isocratic elution utilizing a postcolumn reaction with cerium(IV) and fluorescence detection", Journal of Chromatography A, 2002, 77-84.

Narinder, et al., "Benzimidazole-Based Tripodal Receptor: Highly Selective Fluorescent Chemosensor for Iodide in Aqueous Solution", Organic Letters, 2007, 1991-1994.

Nifiatis, et al., "Comparison of the Photophysical Properties of a Planar, PtOEP, and a Nonplanar, PtOETPP, Porphyrin in Solution and Doped Films", The Journal of Physical Chemistry A, 2011, 13764-13772.

Samaneh, et al., "A highly sensitive and selective turn-on fluorescence sensor for iodide detection based on newly synthesized oligopyrrole derivative and application to real samples", Sensors and Actuators B, 2014, 76-82.

Nozik, et al., "Introduction to Solar Photon Conversion", Chem. Rev. (Washington, D.C., U.S.), 110, 2010, 6443-6445.

Nyarko, et al., "Fluorescence and phosphorescence spectra of Au(III), Pt(II) and Pd(II) porphyrins with DNA at room temperature", Inorganica Chimica Acta 357, 2004, 739-745.

Ou Zhongping, et al., "First electrogeneration of a platinum (IV) porphyrin: elucidation of the PtII/IV and PtIV/II oxidation-reduction processes in nonaqueous media", Jul. 22, 2010, 11272-11276.

Pienpinijtham, et al., "Highly Sensitive and Selective Determination of Iodide and Thiocyanate Concentrations Using Surface-Enhanced Raman Scattering of Starch-Reduced Gold Nanoparticles", American Chemical Society, 2011, 3655-3662.

Sebastiano, "Evolutionary Significance of Iodine", Current Chemical Biology, 2011, 155-162.

Rosspeintner, "Ultrafast Photochemistry in Liquids", Department of Physical Chemistry, University of Geneva, CH-1211 Geneve 8, Switzerland, 2013, 247-271.

Shin-Chun, et al., "Selective Detection of Iodide and Cyanide Anions Using Gold-Nanoparticle-Based Fluorescent Probes", American Chemical Society, 2012, 2652-2658.

Sun, et al., "Generation of Multiple Excitons in Ag2S Quantum Dots: Single High-Energy versus Multiple-Photon Excitation", The Journal of Physical Chemistry Letters, 2014, 659-665.

Stamplecoskie, et al., "Dual nature of the excited state in organic-inorganic lead halide perovskites", Energy & Environmental Science, 2015, 208-2015.

Strozik, et al., "Radiolysis of 5,10,15,20-tetrakis(N-methyl-4-pyridyl)-porphyrin or 5,10,15, 20-tetrakis(4-sulfonatophenyl)-porphyrin in aqueous solution in the presence and in the absence of DNA or human serum albumin", Radiation Physics and Chemistry 91, 2013, 156-165.

Toh, et al., "Electrochemical quantification of iodide ions in synthetic urine using silver nanoparticles: a proof-of-concept", The Royal Society of Chemistry, 2014, 3986-3990.

Yi Xiao, et al., "Conjugated polyelectrolyte-stabilized silver nanoparticles coupled with pyrene derivative for ultrasensitive flourescent detection of iodide", Talanta 131, 2015, 678-683.

Xu, et al., "A reversible fluorescent logic gate for sensing mercury and iodide ions based on a molecular beacon", The Royal Society of Chemistry, 2013, 5281-5287.

Xiu-Hua, et al., "A colorimetric method for highly sensitive and accurate detection ofiodide by finding the critical color in a color change process using silver triangular nanoplates", Analytica Chimica Acta 798, 2013, 74-81.

Xinyan, et al., "Silver nanoplates-based colorimetric iodide recognition and sensing using sodium thiosulfate as a sensitizer", Analytica Chimica Acta 825, 2014, 57-62.

Vaida, et al., "Femtosecond time-resolved photodissociation dynamics of methyl halide molecules on ultrathin gold films", Beilstein Journal of Nanotechnology, 618-627, 2011.

Vauthey, "Investigations of bimolecular photoinduced electron transfer reactions in polar solvents using ultrafast spectroscopy", Journal of Photochemistry and Photobiology A: Chemistry 179, 2006, 1-12.

(56) References Cited

PUBLICATIONS

Vergeldt, et al., "Intramolecular Interactions in the Ground and Excited State of Tetrakis (N-methylpyridyl) porphyrins", J. Phys. Chem., 1995, 4397-4405.

Wolfram, et al., "Gel Electrophoresis Coupled to Inductively Coupled Plasma-Mass Spectrometry Using Species-Specific Isotope Dilution for Iodide and Iodate Determination in Aerosols", Anal. Chem., 2007, 1714-1719.

Wygladacz, et al., "Fluorescent microsphere fiber optic microsensor array for direct iodide detection at low picomolar concentrations", The Royal Society of Chemistry, 2007, 268-272.

"Anion Coordination Chemistry", Angew. Chem. Int. Ed. 2012, 51, 4003.

Beard, "Variations in the Quantum Efficiency of Multiple Exciton Generation for a Series of Chemically Treated PbSe Nanocrystal Films", Nano Letters, vol. 9, No. 2, Jan. 26, 2009, 836-845.

Nozik, et al., "Semiconductor Quantum Dots and Quantum Dot Arrays and Applications of Multiple Exciton Generation to Third-Generation Photovoltaic Solar Cells", Chem. Rev., 110, Oct. 14, 2010, 6873-6890.

Smit, et al., "Expression of the human sodium/iodide symporter (hNIS) in xenotranslanted human thyroid carcinoma", Exp Clin Endocrinol Diabetes 109, 2001, 52-55.

\* cited by examiner

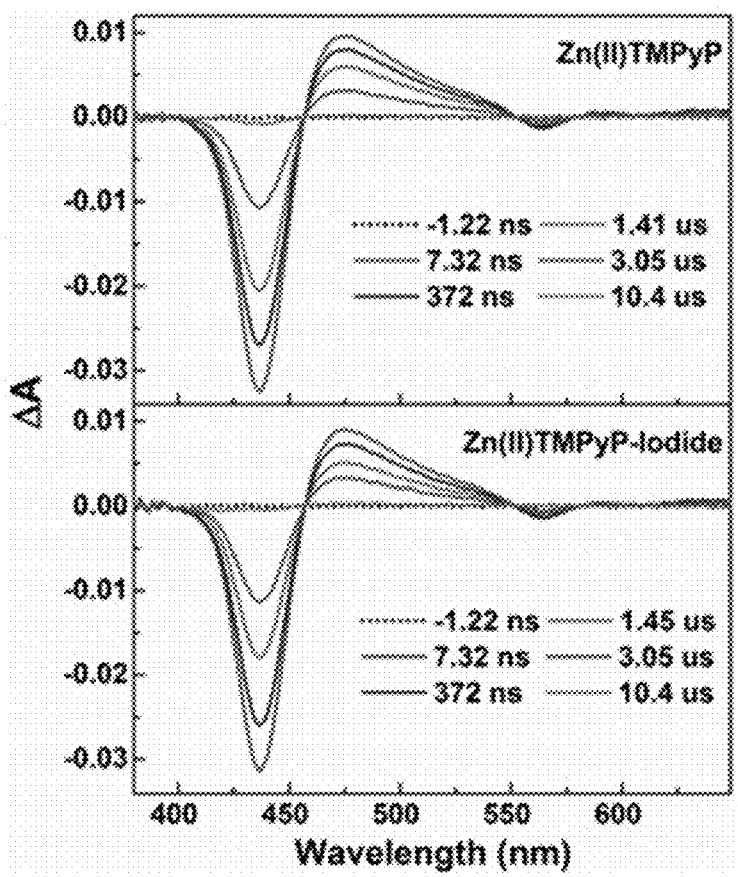
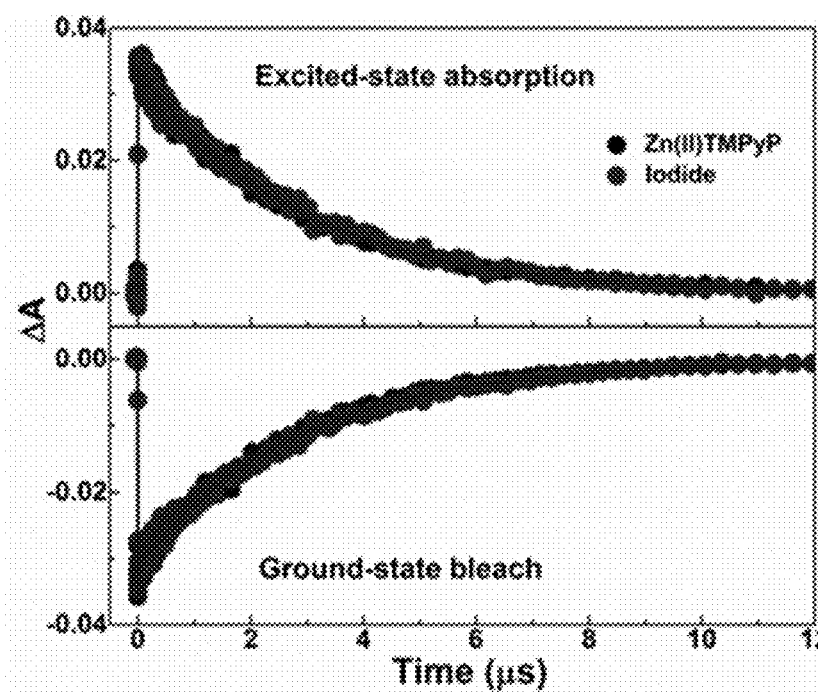
Fig. 11A
Fig. 11B

METHODS AND SYSTEMS FOR MEASURING ANIONS

CROSS-REFERENCE TO RELATED APPLICATIONS

This application claims the benefit of and priority to U.S. Provisional Application Ser. No. 62/115,354, having the title "Methods and Systems for Measuring Anions," filed on Feb. 12, 2015, the disclosure of which is incorporated herein in by reference in its entirety.

BACKGROUND

Anions play a pivotal role in biological, chemical and environmental processes, and they have begun to receive increased attention. Among anions, iodide is of special note not only because of its physiological importance in controlling metabolic activities but also as an essential factor in energy conversion processes. Both deficiency and excess of iodide can result in malfunction and disorders in the human body. In addition to its environmental and biological importance, iodide is a key component of a redox couple often used in solar-energy-harvesting systems. Various methods can be used for the determination of iodide, including photoluminescence, colorimetric detection, time-resolved absorption techniques, mass spectrometry, chromatography, Raman scattering and electrochemical profiling. However, because of its large size and weakly basic nature, the binding capacity of iodide is the weakest among the halide ions. Therefore, the development of a simple, rapid, direct and economical method for the determination of iodide is still under investigation.

Researchers have recently demonstrated high interest in the development of photoluminescence-based methods for the highly sensitive, rapid and selective determination of iodide. However, the complex preparation of the fluorophores, their low hydrophilicity, and the fact that the multistep determination of iodide usually involves a toxic reagent (Hg) has hampered the widespread application of photoluminescence-based methods.

SUMMARY

Embodiments of the present disclosure provide for methods for detecting the presence and/or concentration of anions in a solution, systems for detecting the presence and/or concentration of anions in a solution, anion sensor systems, and the like.

An embodiment of the present disclosure includes a method of detecting anions, including: mixing a solution including an anion with a Pt(II) porphyrin; irradiating the solution with visible light; measuring a photoluminescence signal from the Pt(II) porphyrin; and determining the presence of the anion. In an embodiment, the anion can be selected from the group consisting of: a halogen anion, a sulfide anion, and a cyanide anion.

An embodiment of the present disclosure includes a sensor system, including: a structure having a Pt(II) porphyrin disposed on the surface; a compartment including a solution including an anion, wherein the anion and Pt(II) porphyrin interact to quench the photoluminescence of the Pt(II) porphyrin once the structure is placed in the compartment with the solution; a system for irradiating the solution with visible light; and a system for measuring a signal selected from a photoluminescence signal, UV-Vis signal, or a combination thereof, wherein a change in the signal relative to a signal without the anion present is correlated to the concentration of the anion in the solution.

An embodiment of the present disclosure includes a method, including: placing a structure having a Pt(II) porphyrin disposed on the surface in a compartment including a solution including an anion, wherein the anion and Pt(II) porphyrin interact to quench the photoluminescence of the Pt(II) porphyrin; irradiating the solution with visible light; and measuring a signal selected from a photoluminescence signal, UV-Vis signal, or a combination thereof, wherein a change in the signal relative to a signal without the anion present is correlated to the concentration of the anion in the solution.

Other systems, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

FIGS. 11A-B show transient absorption spectra (11A), and kinetics (11B) for Zn(II)TMPyP porphyrin, and upon its interaction with iodide in aqueous phase ($\lambda_{ex}$=350 nm; $\lambda_{monitoring}$ 350-900 nm), excitation energy density=0.36 mJ/cm$^2$. Monitoring wavelengths are 470 nm for excited-state absorption and 440 nm for ground-state bleach.

Figure 12:
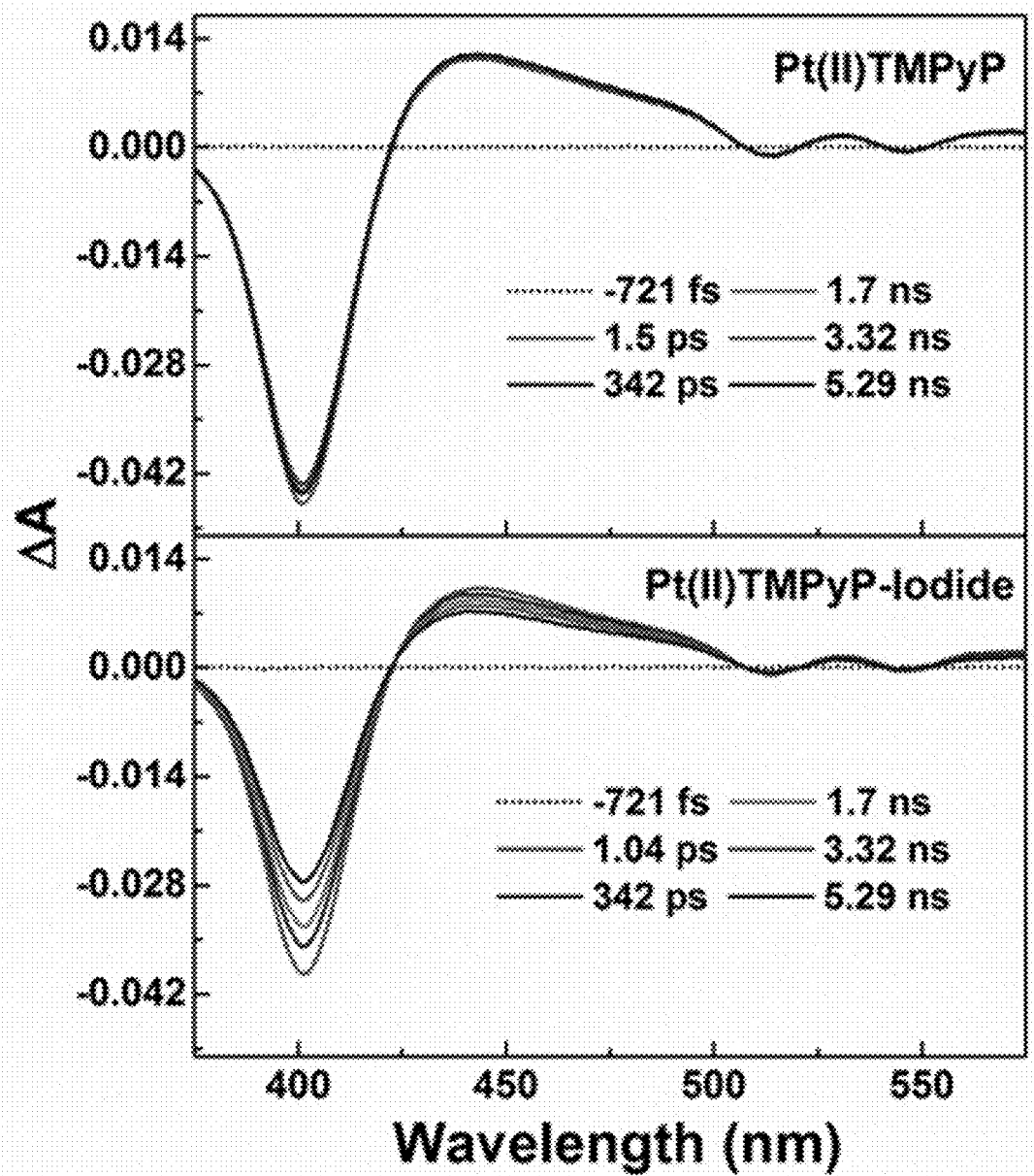

FIG. 12 shows femtosecond transient absorption spectra of Pt(II)TMPyP porphyrin, and with addition of iodide in aqueous phase ($\lambda_{ex}$=350 nm; $\lambda_{monitoring}$ 350-700 nm), excitation energy density=1.44 mJ/cm$^2$.

Figure 13:
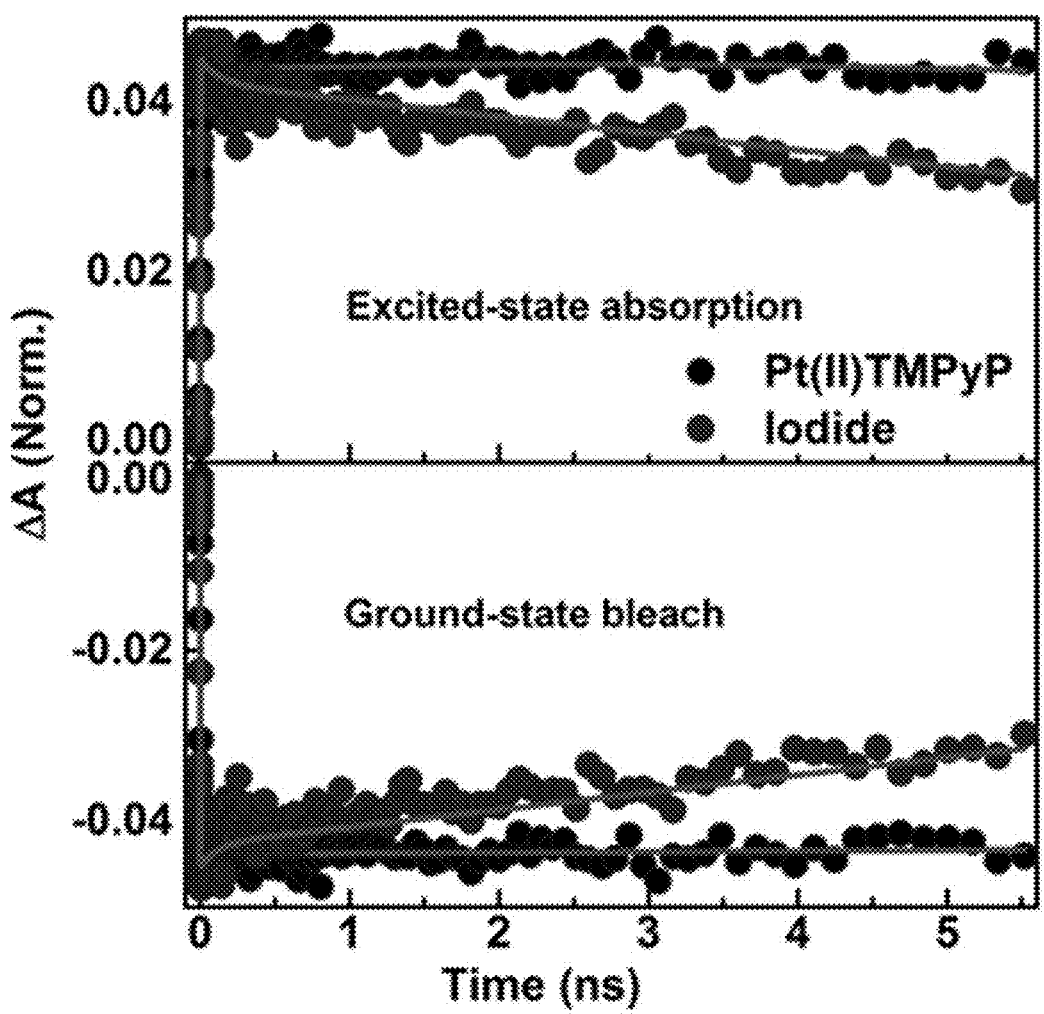

FIG. 13 shows the kinetics of femtosecond transient absorption spectra of Pt(II)TMPyP porphyrin, and with addition of iodide in aqueous phase. Monitoring wavelengths are 443 nm for excited-state absorption and 401 nm for ground-state bleach.

Figure 14:
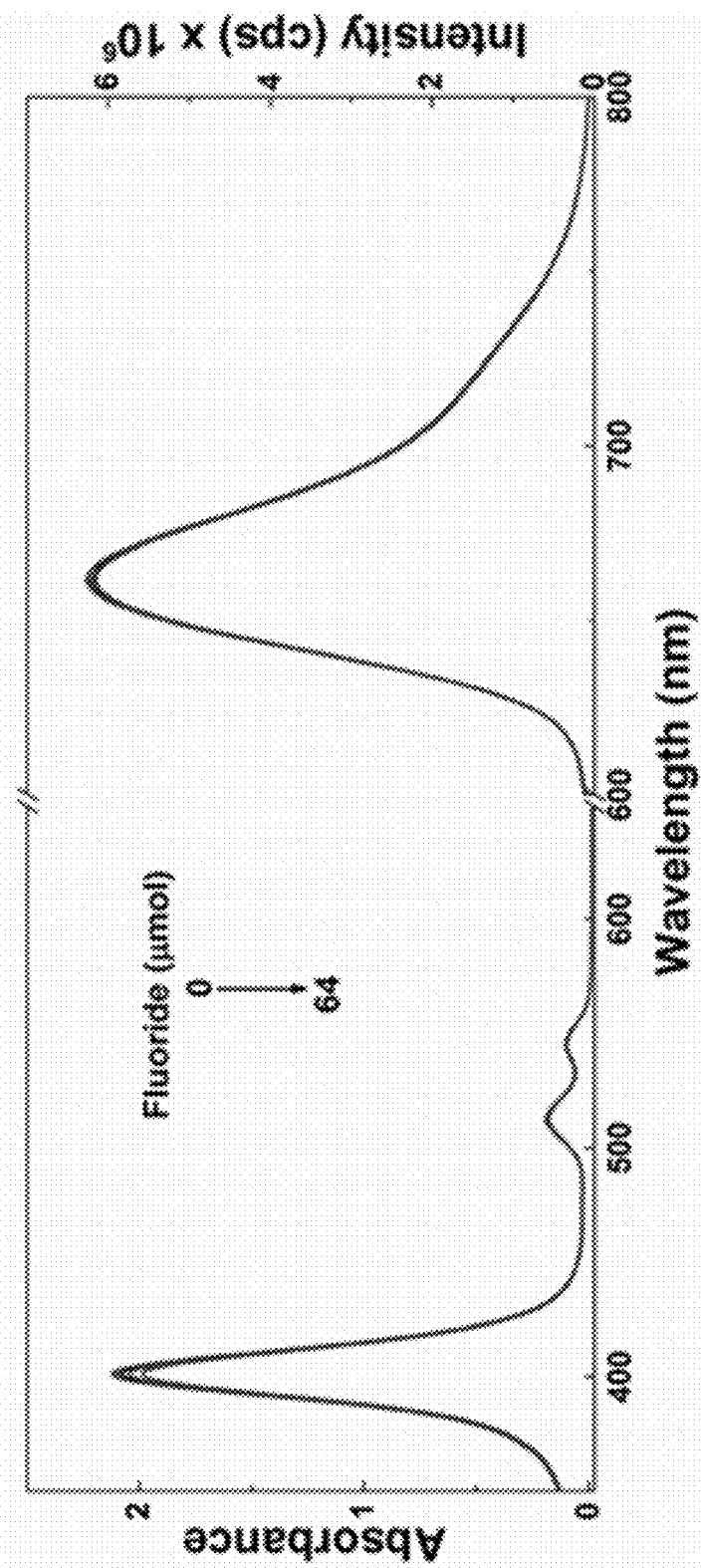

FIG. 14 shows steady-state UV-Vis absorption (left), and photoluminescence (right, $\lambda_{ex}$=512 nm) spectra for Pt(II) TMPyP, and after successive additions of fluoride in aqueous phase.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

General Discussion

Embodiments of the present disclosure provide for methods for detecting the presence and/or concentration of anions in a solution, systems for detecting the presence and/or concentration of anions in a solution, anion sensor systems, and the like. Embodiments of the present disclosure can be used in the biomedical field, pharmaceutical field, food and beverage field, environmental field, solar harvesting systems, oil and gas field, petrochemical research, industrial field, and the like, to determine the presence of an anion(s) and measure the concentration of the anion(s).

Embodiments of the present disclosure provide for an easy and rapid method for ultrasensitive detection of low pico-mole (ppt; parts per trillion) levels of anions such as iodide in solution such as in the aqueous phase. An embodiment of the present disclosure provides for a non-toxic porphyrin sensor for easy, rapid and economical detection of trace levels of an anion such as iodide upon directing light onto the solution. In particular, an embodiment provides the ability to generate photoluminescence spectra and the linear change of intensity with addition of iodide ions can be determined. Furthermore, studies were performed to understand the photo-physics of the phenomenon and its relation to the specific composition of the porphyrin. Additional details and embodiments are provided in the following Examples.

An embodiment of the present disclosure includes methods that include a single step direct technique for monitoring an anion(s) in a solution (e.g., aqueous phase) with picomole detections capabilities.

An embodiment of the present disclosure includes a method of detecting anions. In an embodiment, the anions can include a halogen anion (e.g., iodide), a sulfide anion, and a cyanide anion. In general, the method includes mixing a solution including an anion with a Pt(II) porphyrin. In an embodiment, the Pt(II) porphyrin can include 5, 10, 15, 20-tetra(1-methyl-4-pyridino)-porphyrin (Pt(II) tetrachloride, analogues thereof, derivatives thereof, and the like. In an embodiment, the anions and Pt(II) porphyin can be dissolved in a solution such as water, methanol, DMSO, acetonitrile, combinations thereof, and the like.

Subsequently, the solution can be irradiated with visible light. The photoluminescence signal from the Pt(II) porphyrin can be measured and the photoluminescence signal can be correlated with the presence and/or concentration of the anion. In an embodiment, a combination of anions can be detected and the concentration measured. In an embodiment, a UV-Vis signal can be measured as well and correlated to the presence and concentration of one or more anions.

In an embodiment, the method includes placing a structure (e.g., test strip) having a Pt(II) porphyrin disposed on the surface into a compartment including a solution including an anion. Once the structure is placed into the compartment (e.g., cuvette, a test tube, beaker, or the like), the anion and Pt(II) porphyrin interact to quench the photoluminescence of the Pt(II) porphyrin. Next, the solution is irradiated with visible light. Thereafter, a signal is measured. In an embodiment, the signal can be a photoluminescence signal and/or a UV-Vis signal. A change in the signal relative to a signal without the anion present is correlated to the concentration of the anion in the solution.

More particularly, in the presence of an anion such as iodide, the quenching of the photoluminescence of the Pt(II) porphyin can be monitored upon irradiation with visible light. This method does not require complex preparatory steps or additional species such as Hg, which is often used for the activation of fluorophores.

Ultrafast laser spectroscopy or similar spectroscopy or techniques can be used to measure the quenching of the photoluminescence. Different anions can quench to different magnitudes. The detection limit can be determined using the $3\sigma$ IUPAC method, where the detection limit=$3\sigma$/slope. In an embodiment, a calibration curve for photoluminescence intensity against anion concentration can be used to determine the concentration. The slope value was taken from the curve, and the standard deviation $\sigma$ was calculated for the photoluminescence intensity of the blank Pt(II)TMPyP solution in the absence of the anion. In this way, the concentration can be determined. In an embodiment, the anion can be detected at a level of about 20 to 50 pmol or about 30 pmol in the solution, while in some embodiments the anion can be detected to levels down to about 20 pmol or down to about 30 pmol.

In addition to measuring the quenching of the photoluminescence, UV-Vis spectra also illustrated a decrease in the optical absorbance. In this way, each anion can have its own unique "signature" (e.g., photoluminescence spectra and UV-Vis spectra) that can be used to differentiate various anions. In an embodiment, calibration curves can be constructed for different anions for the photoluminescence spectra and/or UV-Vis spectra and can be used to identify the anion(s) and determine the concentration of the anions in the solution.

An embodiment of the disclosure also includes a sensor system. In an embodiment, the sensor system includes a structure having a Pt(II) porphyrin disposed on the surface or alternatively, the Pt(II) porphyrin can be a solid or liquid that is mixed with the solution of interest. In addition, the sensor system includes a compartment including a solution including an anion. The anion and Pt(II) porphyrin can interact to quench the photoluminescence of the Pt(II) porphyrin. The sensor system can include a system for irradiating the solution with visible light (e.g., an irradiation system). The sensor system can also include a system for measuring a signal (e.g., a photoluminescence signal and UV-Vis signal). As described above and in the example, a change in the signal relative to a signal without the anion(s) present can be correlated to the concentration of the anion(s) in the solution. Additional details and embodiments are provided in the following Examples.

In an embodiment, a Pt(II) porphyrin based photoluminescence sensor (e.g., a 5,10,15,20-tetra(1-methyl-4-pyridino)-porphyrin Pt(II) tetrachloride (Pt(II)TMPyP)-based photoluminescence sensor) was used for the ultra-sensitive and rapid determination of an anion (e.g., iodide). An embodiment of the method allows for use of a one-step direct technique for monitoring iodide in an aqueous phase with a pico-mole (pmol) detection limit. In a particular embodiment where the anion is iodide, iodide can be used to quench photoluminescence of Pt(II)TMPyP and can be directly monitored upon irradiation with visible light. The sensor and method do not use hazardous materials like other sensors and techniques while also provide exceptional detection limits in a short amount of time.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

In this study, we not only provide a simple method with a previously unattained ($1\times10^{-12}$ M) detection limit in aqueous solution but also propose a detailed mechanism for photoluminescence quenching using cutting-edge ultrafast laser spectroscopy with broadband capabilities. Interestingly, a control experiment using Zn(II)TMPyP clearly indicated that the Pt metal center is the element for the quenching and the extremely low detection limit.

Both of the investigated porphyrins, Pt(II)TMPyP and Zn(II)TMPyP, were supplied by Frontier Scientific. High-purity halide salts of $NH_4F$, NaCl, KBr and KI were purchased from Sigma-Aldrich. Porphyrins and halide salts were completely dissolved in Milli-Q water, and all spectral measurements were performed without any additions. Absorption spectra were recorded on a Cary 6000i UV-Vis-NIR spectrophotometer (Varian, Inc.). Steady-state photoluminescence spectra were recorded with a Jobin-Yvon-Horiba Fluoromax-4 spectrofluorometer. We utilized femto- and nanosecond transient absorption spectroscopy to probe the photophysical processes that occur upon the photoexcitation of the Pt(II)TMPyP with and without iodide. The experimental setup is detailed elsewhere.[47-49]

Figure 1:
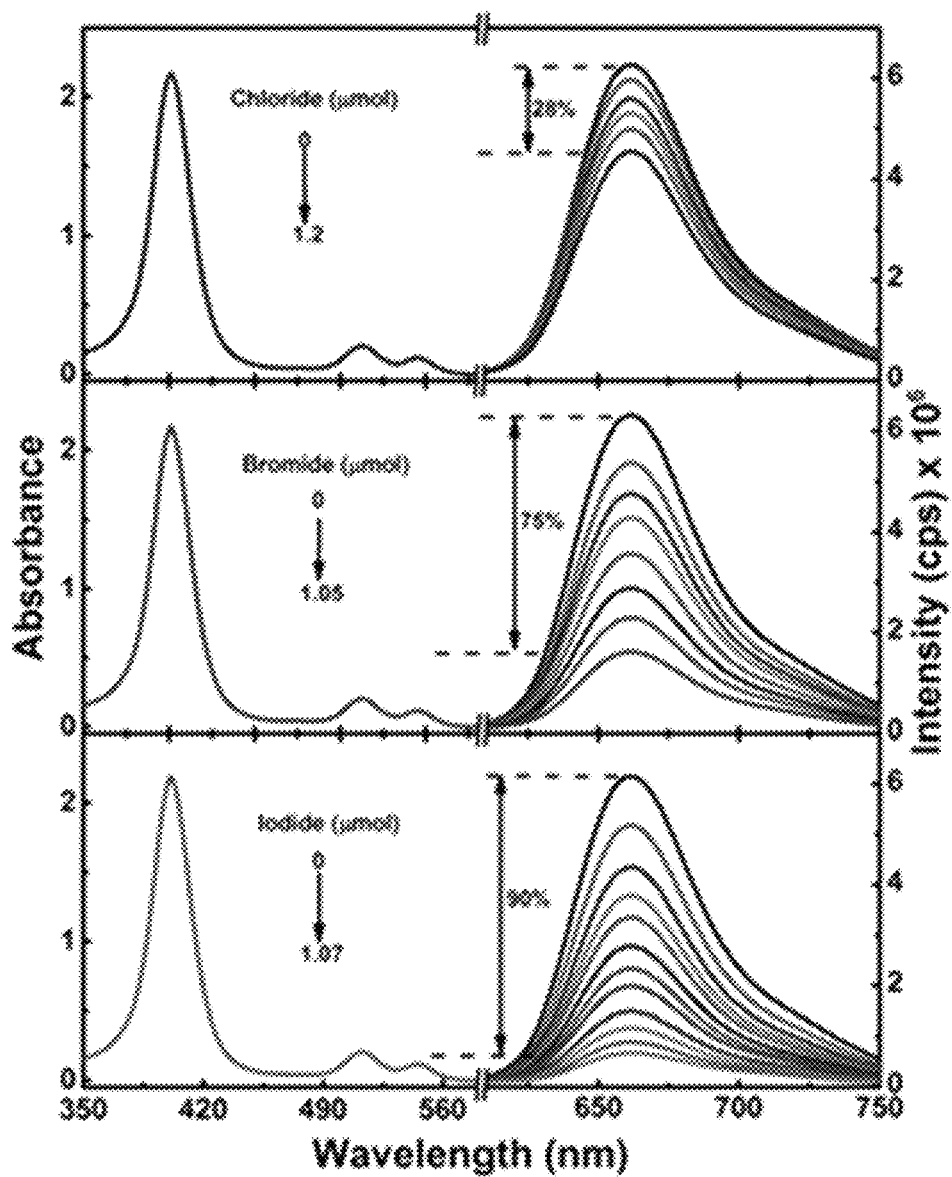
FIG. 1 shows absorption (left) and photoluminescence (right, λex=512 nm) spectra of Pt(II)TMPyP before and after the additions of chloride, bromide and iodide in the aqueous phase.

FIG. 1 displays the steady-state absorption and photoluminescence spectra of Pt(II)TMPyP alone and with various halide ions, i.e., chloride, bromide and iodide. Three milliliters of 12.8 µM Pt(II)TMPyP aqueous solution was added to a quartz cuvette with a 1 cm path length, and an aqueous solution of a halide ion was then added. Samples were excited at 512 nm, and the aperture size for both the entrance and exit slits was kept the same for all experiments. The obtained emission agrees in shape and position to previously reported Pt(II) porphyrin emission which is mainly due to heavy atom effect of Pt(II) as central atom leading to efficient intersystem crossing (ISC).[50, 51] As evident in FIG. 1 (left panel), the change in peak intensity and position in the absorption spectrum of Pt(II)TMPyP after halide addition was negligible. In contrast, a significant intensity quenching in the photoluminescence spectrum upon halide ion addition is clearly evident in the figure. The quenching magnitude for the different halides decreased in the order iodide>bromide>chloride. The addition of 1.2 µmol of chloride led to approximately 28% quenching of the photoluminescence of Pt(II)TMPyP, and the extent of quenching increased down the halogen group, with almost 75 and 90% quenching observed after the additions of similar amounts of bromide (1.05 µmol) and iodide (1.07 µmol), respectively. It is worth mentioning that fluoride didn't show any significant tendency to interact with Pt(II)TMPyP (see FIG. 14).

The literature contains only a few reports on the ultra-trace, low-pmol-level detection of iodide. Wygladacz et al. reported a fluorescent microsphere fiber optic microsensor array for the low-pmol detection of iodide.[29] However, the microsensor exhibited the lowest limit of detection of 3 pmol only at pH 3.5. Recently, Dasary et al. reported a surface-enhanced Raman scattering probe for ultra-sensitive detection.[43] An iodide detection limit of 30 pmol was demonstrated on the basis of indirect Raman intensity originating from the desorption of rhodamine from gold nanoparticles.

Figure 5:
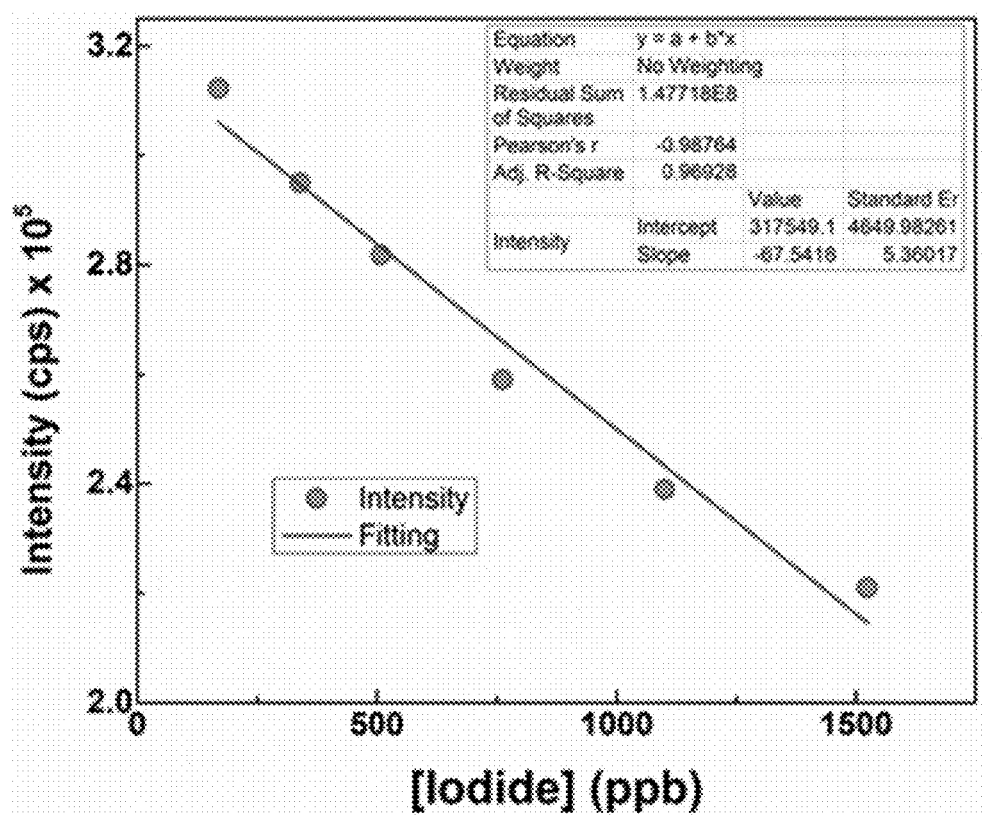
FIG. 5 plots the relation of photoluminescence intensity against the iodide added into Pt(II)TMPyP and linear fit for estimation of detection limit.

The detection limit was determined from our photoluminescence quenching results using the 3σ IUPAC method, where the detection limit=3σ/slope.[20, 24, 26, 33, 36] A calibration curve for photolumine-scence intensity against iodide concentration was first constructed (FIG. 5). The slope value was taken from the curve, and the standard deviation σ was calculated for the photoluminescence intensity of the blank Pt(II)TMPyP solution in the absence of iodide. Interestingly, a never-before-attained detection limit of 1 pmol was obtained.

The photoluminescence quenching upon the addition of halides indicates the presence of a photoinduced electron transfer event between the halide donor and the Pt(II)TMPyP acceptor. Stern-Volmer plots for all of the halide ions show a deviation from linearity with Pt(II)TMPyP (FIGS. 6 and 7), indicating that a static reaction is involved in the quenching process. The observed negative deviation from linearity in Stern-Volmer plots at very high halide concentration can be attributed to the formation of a luminescent exciplex between the negatively charged halide and the poor electron density on the Pt metallic center (explained below in transient measurements).[52] From the relationship $K_{SV}=k_q\tau^\circ$,[53] where $K_{SV}$ is the Stern-Volmer constant, $k_q$ is the bimolecular quenching rate constant and $\tau^\circ$ is the phosphorescence lifetime of Pt(II)TMPyP (1.03 µs), we calculated $k_q \approx 7.8 \times 10^{12}$ M$^{-1}$s$^{-1}$. This quenching rate far exceeds the diffusion-controlled limit (the estimated rate for iodide diffusion for an aqueous sample under the current experimental conditions is $\sim 3 \times 10^{10}$ M$^{-1}$s$^{-1}$, as determined using the Stokes-Einstein equation),[54] establishing the fact that the quenching is due to the static interaction between the donor-acceptor components. To confirm the static quenching, the phosphorescence lifetimes of the Pt(II)TMPyP free and in the presence of different iodide concentrations giving 30, 50, and 70% quenching were measured; the results are displayed in FIG. 8. The time decay curves collected for the four solutions exhibited the same lifetime, confirming the static nature of the quenching mechanism.[53] Further confirmation of the static nature of the quenching mechanism is indicated by the similarity of the Stern-Volmer quenching constants for samples in water and methanol (see FIG. 9). Despite the different viscosities of water and methanol, the $K_{SV}$ values extracted for the iodide interaction with Pt(II)TMPyP in methanol is 8.6 µM$^{-1}$ and that in water is 8.01 µM$^{-1}$. The similarity between these values suggests that quenching does not depend on solvent viscosity, which favors a static-interaction explanation.

Figure 10:
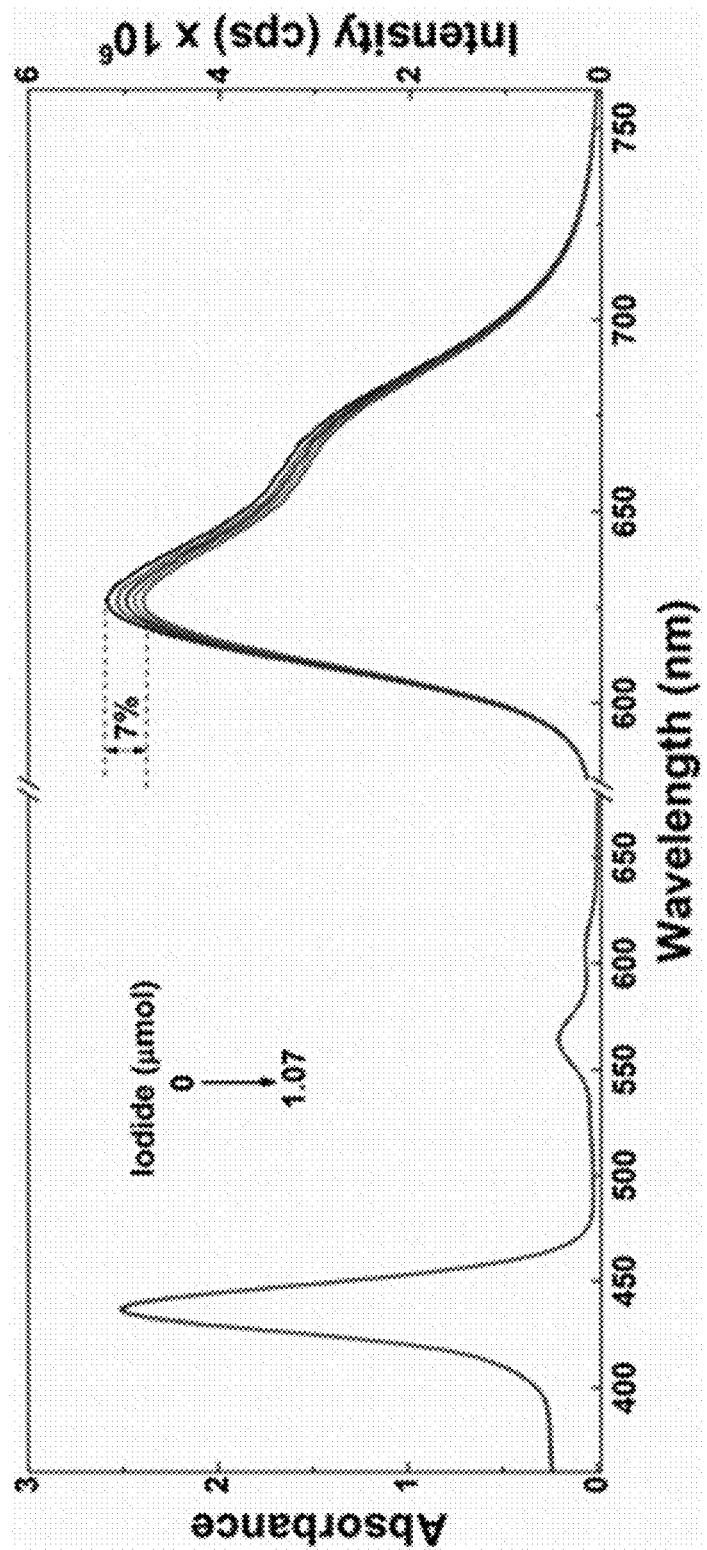
FIG. 10 shows UV-Vis absorption (left), and photoluminescence (right, $\lambda_{ex}$=563 nm) spectra for Zn(II)TMPyP and after successive additions of iodide in aqueous phase.

Similar to the Pt(II)TMPyP and iodide system, 1.07 µmol of iodide was sequentially added to 3 mL of 12.7 µM Zn(II)TMPyP. The steady-state and excited-state absorptions remained essentially the same before and after the iodide addition (FIGS. 10 and 11A-B). For the photoluminescence measurements of Zn(II)TMPyP with the addition of 1.07 µmol iodide, in contrast to the 90% photoluminescence quenching observed in the iodide-Pt(II)TMPyP mixture, only approximately 7% quenching was observed (FIG. 10). This quenching behavior demonstrates that the change in the photoluminescence was specific to the metal center in the cavity of the porphyrin and pertained to its emissive state, as discussed below.

Figure 2:
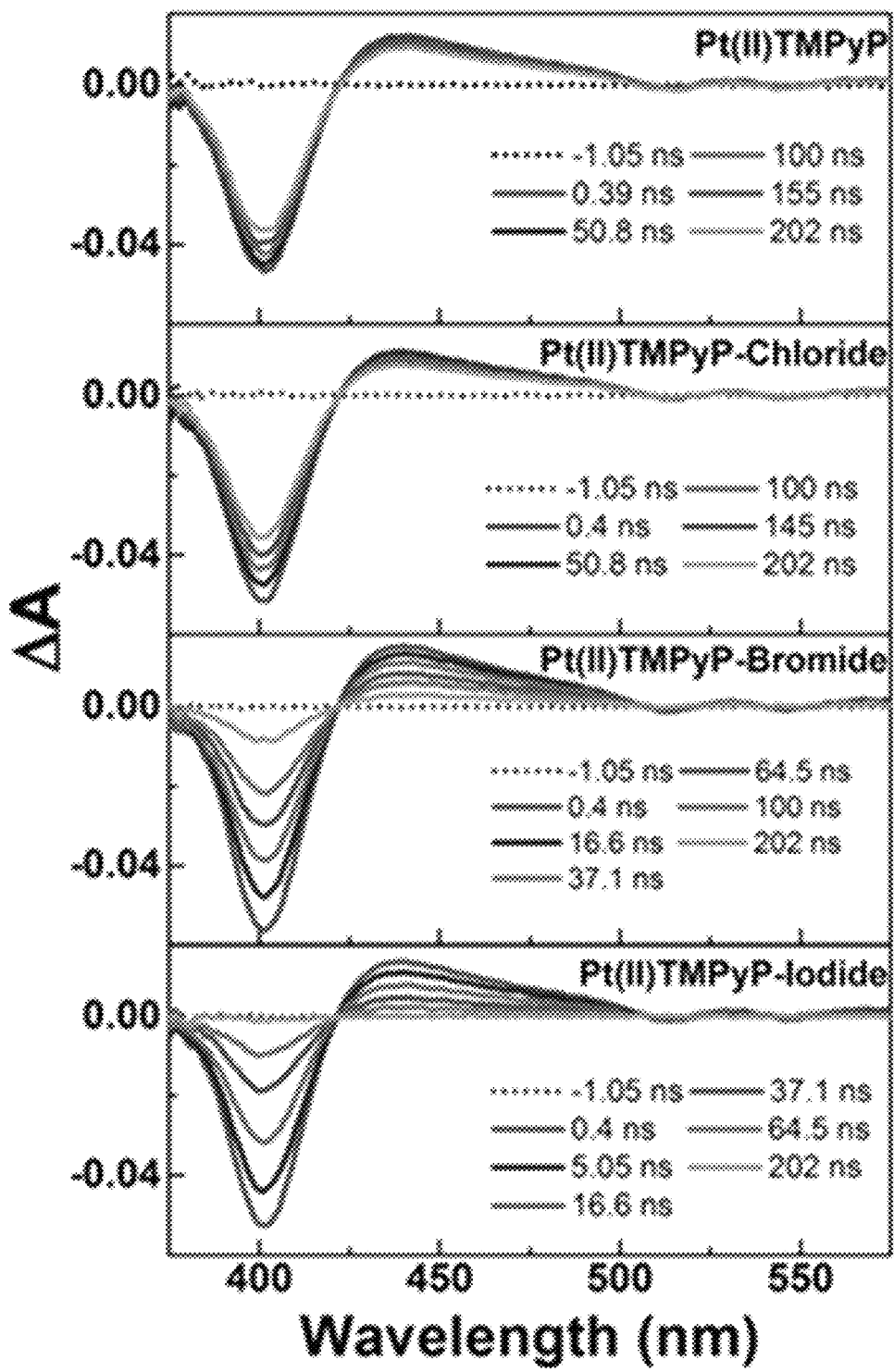
FIG. 2 shows the transient absorption spectra of Pt(II)TMPyP before and after successive additions of chloride, bromide and iodide in the aqueous phase ($\lambda_{ex}$=350 nm; $\lambda_{monitoring}$=350-900 nm), excitation energy density of 2.17 mJ/cm$^2$.

Transient absorption (TA) spectroscopy is an essential method for investigating photoinduced excited-state interactions.[55-57] In the present work, the excited-state interaction of halides with Pt(II)TMPyP was examined using nanosecond (ns) and femtosecond (fs) TA spectroscopy. The recorded ns-TA spectra of aqueous solutions of free Pt(II)TMPyP and its mixtures with chloride, bromide, and iodide collected after 350 nm photoexcitation are shown in FIG. 2.

The ns-TA spectra for Pt(II)TMPyP with and without halides show ground-state bleaching at ~400 nm and excited-state $T_1$-$T_n$ absorption over the range 420-600 nm. These spectral features are consistent with the reported excited-state triplet absorption for porphyrin molecules.[58, 59] Members of this class of porphyrins in which Pt is the central atom are known to exhibit a very rapid and efficient singlet-to-triplet ($S_1 \rightarrow T_1$) intersystem crossing associated with strong spin-orbit coupling.[60] The TA spectra for Pt(II)TMPyP show a change over a time window of up to 4 µs, which is in agreement with the reported triplet lifetime of aerated solutions (~1 µs).[58] The TA spectra recorded in the presence of halides demonstrate a significant shortening of the time window. Moreover, the time window over which TA spectra are detected shows a further shortening in the same order of chloride>bromide>iodide. The kinetic traces collected from the TA spectra at both the ground-state bleach recovery and the excited-state absorption decay are given in FIG. 3.

All kinetic traces both for ground-state bleach and excited-state decay are fitted to single exponent fitting curves as shown in the figure. The ground-state bleach recovery extracted from the TA spectra of Pt(II)TMPyP in the presence of the halides decreases in the order of Pt(II)TMPyP (1.03 µs)>Pt(II)TMPyP-chloride (0.56 µs)>Pt(II)TMPyP-bromide (0.09 µs)>Pt(II)TMPyP-iodide (0.04 µs). This overall fast deactivation of the triplet signal implies the presence of an extra process involved in deactivation of the excited state when halides are present compared to the case of free Pt(II) porphyrin. Notably, the ring reduction potential of Pt(II) porphyrin to be in the range of −1.39 to −1.3,[61] whereas the oxidation potentials of the halides ($X^{31}$/X) are 1.36, 1.087, and 0.535 for chloride, bromide, and iodide, respectively.[62] The fast changes in the TA spectra, the redox properties and the lack of any possibility for energy transfer suggests a photoinduced electron transfer from the halides to the Pt(II)TMPyP*. In general, a peripheral substituent at the meso position on a porphyrin macrocycle can significantly change its electrochemical potential.[63]

In this regime, the electron-accepting positively charged pyridinium units ($CH_3$—$N^+$) on the meso positions of the porphyrin will extract the electron density from the porphyrin macrocycle via intramolecular charge transfer (ICT).[64] If we consider the ICT in conjunction with the Pt(II) as the central atom in the TMPyP core, Pt-to-porphyrin back electron donating ($d \rightarrow e_g(\pi^*)$)[50, 65] produces a region of poor electron density on the Pt metallic center. This generation of this region is expected to facilitate the axial electron transfer interaction with the Pt central atom. Hence, upon photoexcitation, an attractive center is anticipated to be formed around the Pt in the center of the Pt(II)TMPyP, which, in turn, facilitates attraction of the negatively charged halides, triggering electron transfer. Notably, the strong spectral overlap between the porphyrin anion radical, which is reported to occur at 470 nm, and $T_1$-$T_n$ TA and the very low concentration of halide used in these experiments make monitoring of the anion radical absorption difficult.[66]

To confirm the importance of Pt as the central atom in the suggested mechanism, a control experiment was carried out using Zn(II)TMPyP with iodide; in this experiment, the TA did not exhibit any change (see FIG. 11A-B), confirming that the interaction occurs with the Pt at the porphyrin macrocycle center. Further confirmation of the fast photoinduced electron transfer was provided by the fs-TA in FIGS. 12 and 13.

Figure 4:
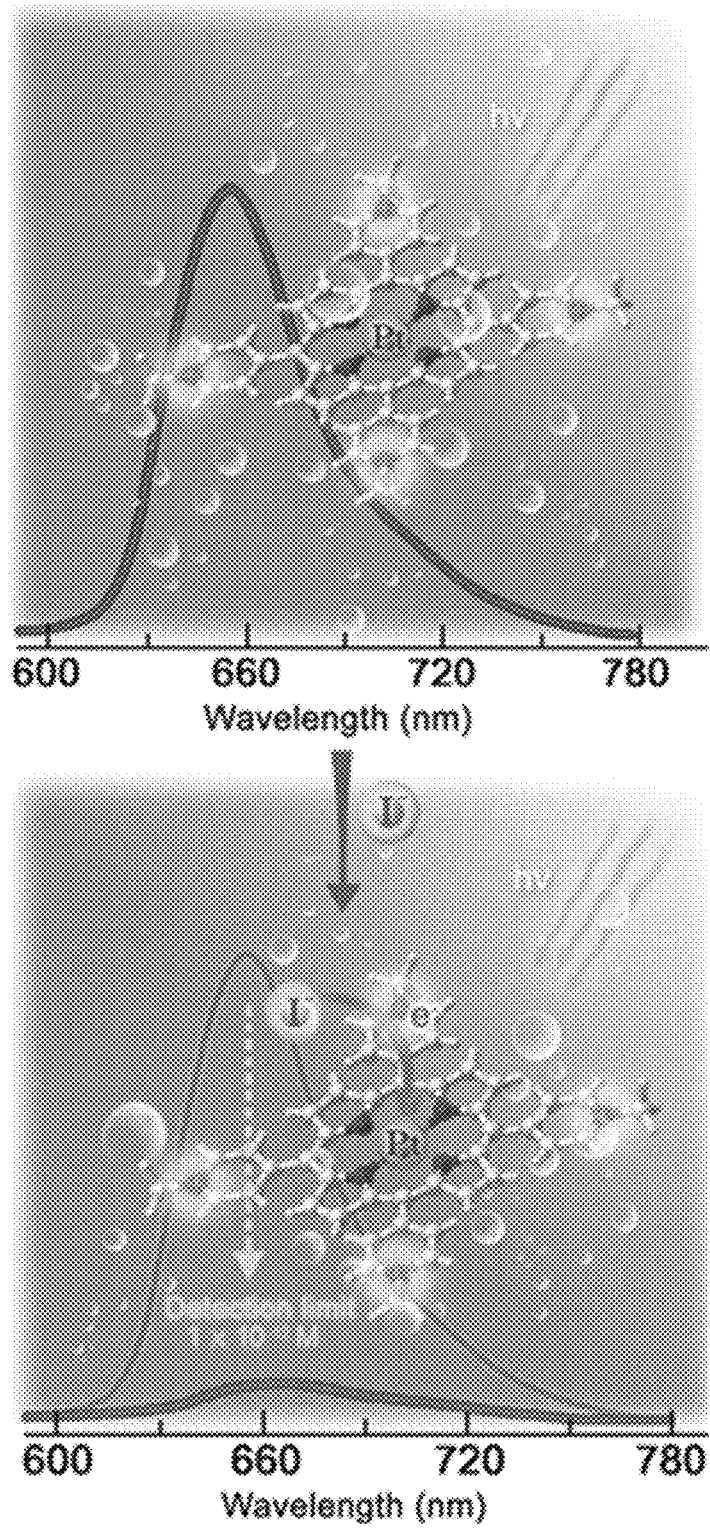
FIG. 4 illustrates luminescence quenching of Pt(II)TMPyP due to photoinduced reduction by iodide in the aqueous phase.

In the case of Pt(II)TMPyP, the triplet-triplet absorption developed within 120 fs, which was the temporal resolution of our experiment. This result is in good agreement with the efficient and fast ISC.[50, 51] On the contrary, the fs-TA for Pt(II)TMPyP in the presence of iodide (see FIG. 13) exhibited a fast change in the ground-state bleach, indicating the rapid deactivation of the excited state because of photoinduced electron transfer between iodide and Pt(II)TMPyP, as simplified in FIG. 4. Taking advantage from this Pt(II) TMPyP-iodide system, further research is going on towards the development of porphyrin-based sensors for other crucial anions like sulfide and cyanide.

CONCLUSIONS

Many halogen containing compounds have come into everyday use in the fields of chemistry, biology, medicine, plastics, food and even photography. Many techniques for the detection of these halogen compounds and ions have been developed not only to reduce the complexity and cost of the analysis but also to improve the detection sensitivity. In these techniques various type of materials namely polymers, porphyrin, nano-particles/clusters, quantum dots, DNA logic gate, and composites have been tried as photoluminescence sensor for the detection of halides.[17-32] Requirement of controlled shape and size makes nano-sized materials less preferred choice as a sensor. Furthermore, deterioration and modification of nano-sized materials also question their application. Herein, we report for the first time the photoinduced triplet-state electron transfer of Pt(II) TMPyP as an easy, rapid, environmentally friendly, ultrasensitive (a never-before-attained detection limit of $1\times10^{-12}$ M) and economical method for the determination of iodide in the aqueous phase. Pt(II) porphyrin phosphorescence was observed to be quenched to different magnitudes through the use of different halides. The efficiency of quenching was experimentally demonstrated to increase in the order chloride<bromide<iodide. The very low concentration range over which the Pt(II) porphyrin exhibit quenching and the simplicity of the measurements constitute the basis for a very safe and efficient halide sensor in the analytical market.

EXAMPLE 1 REFERENCES

1. J. L. Sessler, P. A. Gale and W. S. Cho, *Anion Receptor Chemistry*, The Royal Society of Chemistry, Cambridge, UK, 2006.
2. V. Amendola, L. Fabbrizzi, M. Licchelli and A. Taglietti, *Anion Coordination Chemistry*, Wiley-VCH, Weinheim, 2012.
3. P. A. Gale, N. Busschaert, C. J. E. Haynes, L. E. Karagiannidis and I. L. Kirby, *Chem. Soc. Rev.*, 2014, 43, 205-241.
4. J. W. A. Smit, J. P. Schroder-Van der Elst, M. Karperien, I. Que, J. A. Romijn and D. Van der Heide, *Exp. Clin. Endocrinol. Diabetes*, 2001, 109, 52-55.
5. C. G. Brown, R. F. Harland, I. R. Major and C. K. Atterwill, *Food Chem. Toxicol.*, 1987, 25, 787-794.
6. C. Nasr, S. Hotchandani and P. V. Kamat, *J. Phys. Chem. B*, 1998, 102, 4944-4951.
7. K. G. Stamplecoskie, J. S. Manser and P. V. Kamat, *Energy Environ. Sci.*, 2014, DOI: 10.1039/C4EE02988G, Ahead of Print.
8. B. H. Meekins and P. V. Kamat, *J. Phys. Chem. Lett.*, 2011, 2, 2304-2310.
9. A. J. Nozik and J. Miller, *Chem. Rev.* (Washington, D.C., U. S.), 2010, 110, 6443-6445.
10. A. J. Nozik, M. C. Beard, J. Johnson, M. C. Hanna, J. M. Luther, A. Midgett, O. Semonin and J. Michel, *Prepr. Symp.—Am. Chem. Soc., Div. Fuel Chem.*, 2012, 57, 14.
11. M. Law, J. M. Luther, M. C. Beard, S. Choi and A. J. Nozik, 2009.
12. V. R. Preedy, G. N. Burrow and R. R. Watson, *Comprehensive Handbook of Iodine: Nutritional, Biochemical, Pathological, and Therapeutic Aspects*, Academic Press, New York, 2009.
13. E. Nystrom, G. E. B. Berg, S. K. G. Jansson, O. Torring and S. V. Valdemarsson, *Thyroid Disease in Adults*, berlin, Germany, 2011.
14. S. Venturi, *Curr. Chem. Biol.*, 2011, 5, 155-162.
15. R. Abe, K. Shinmei, N. Koumura, K. Hara and B. Ohtani, *J. Am. Chem. Soc.*, 2013, 135, 16872-16884.
16. C. D. Geddes, *Meas. Sci. Technol.*, 2001, 12, R53-R88.
17. J. M. Fang, P. F. Gao, X. L. Hu and Y. F. Li, *RSC Adv.*, 2014, 4, 37349-37352.
18. Y. Xiao, Y. Zhang, H. Huang, Y. Zhang, B. Du, F. Chen, Q. Zheng, X. He and K. Wang, *Talanta*, 2015, 131, 678-683.
19. M. M. Kruk, Y. B. Ivanova, V. B. Sheinin, A. S. Starukhin, N. Z. Mamardashvili and O. I. Koifman, *Makrogeterotsikly*, 2008, 1, 50-58.
20. L. Wang, G. Fang, D. Ye and D. Cao, *Sens. Actuat. B: Chemical*, 2014, 195, 572-580.
21. J. Liu, Q. Lin, Y.-M. Zhang and T.-B. Wei, *Sens. Actuat. B: Chemical*, 2014, 196, 619-623.
22. S. Nabavi and N. Alizadeh, *Sens. Actuat. B: Chemical*, 2014, 200, 76-82.
23. S. Chen, P. Wang, C. Jia, Q. Lin and W. Yuan, *Spectrochim. Acta A*, 2014, 133, 223-228.
24. S. Hussain, S. De and P. K. Iyer, *ACS AppL Mater. Interfaces*, 2013, 5, 2234-2240.
25. F. Du, F. Zeng, Y. Ming and S. Wu, *Michrochim. Acta*, 2013, 180, 453-460.
26. X. Wu, J. Chen and J. X. Zhao, *Analyst*, 2013, 138, 5281-5287.
27. S.-C. Wei, P.-H. Hsu, Y.-F. Lee, Y.-W. Lin and C.-C. Huang, *ACS Appl. Mater. Interfaces*, 2012, 4, 2652-2658.
28. N. Singh and D. O. Jang, *Org. Lett.*, 2007, 9, 1991-1994.
29. K. Wygladacz and E. Bakker, *Analyst*, 2007, 132, 268-272.
30. H. Zhang, Y. Li, X. Liu, P. Liu, Y. Wang, T. An, H. Yang, D. Jing and H. Zhao, *Env. Sci. Technol. Lett.*, 2013, 1, 87-91.
31. M. S. Mehata and H. B. Tripathi, *J. Luminesc.*, 2002, 99, 47-52.
32. E. Nyarko, N. Hanada, A. Habib and M. Tabata, *Inorg. Chim. Acta*, 2004, 357, 739-745.

33. B. Basumatary, M. Ayoub Kaloo, V. Kumar Singh, R. Mishra, M. Murugavel and J. Sankar, *RSC Adv.*, 2014, 4, 28417-28420.
34. A. Nayal, A. Kumar, R. K. Chhatra and P. S. Pandey, *RSC Adv.*, 2014, 4, 39866-39869.
35. X. Hou, S. Chen, J. Tang, Y. Xiong and Y. Long, *Anal. Chim. Acta*, 2014, 825, 57-62.
36. G. Zhou, C. Zhao, C. Pan and F. Li, *Anal. Meth.*, 2013, 5, 2188-2192.
37. X.-H. Yang, J. Ling, J. Peng, Q.-E. Cao, Z.-T. Ding and L.-C. Bian, *Anal. Chim. Acta*, 2013, 798, 74-81.
38. M. E. Vaida, R. Tchitnga and T. M. Bernhardt, *Beilstein J. Nanotechnol.*, 2011, 2, 618-627.
39. W. Brüchert, A. Helfrich, N. Zinn, T. Klimach, M. Breckheimer, H. Chen, S. Lai, T. Hoffmann and J. Bettmer, *Anal. Chem.*, 2007, 79, 1714-1719.
40. S. Mishra, V. Singh, A. Jain and K. K. Verma, *Analyst*, 2000, 125, 459-464.
41. I. A. Carasel, C. R. Yamnitz, R. K. Winter and G. W. Gokel, *J. Org. Chem.*, 2010, 75, 8112-8116.
42. Y. Miura, M. Hatakeyama, T. Hosino and P. R. Haddad, *J. Chromat. A*, 2002, 956, 77-84.
43. S. S. R. Dasary, P. Chandra Ray, A. K. Singh, T. Arbneshi, H. Yu and D. Senapati, *Analyst*, 2013, 138, 1195-1203.
44. P. Pienpinijtham, X. X. Han, S. Ekgasit and Y. Ozaki, *Anal. Chem.*, 2011, 83, 3655-3662.
45. H. S. Toh, K. Tschulik, C. Batchelor-McAuley and R. G. Compton, *Analyst*, 2014, 139, 3986-3990.
46. F. C. Pereira, L. M. Moretto, M. De Leo, M. V. Boldrin Zanoni and P. Ugo, *Anal. Chim. Acta*, 2006, 575, 16-24.
47. A. O. El-Ballouli, E. Alarousu, M. Bernardi, S. M. Aly, A. P. Lagrow, O. M. Bakr and O. F. Mohammed, *J. Am. Chem. Soc.*, 2014, 136, 6952-6959.
48. A. O. El-Ballouli, E. Alarousu, A. Usman, J. Pan, O. M. Bakr and O. F. Mohammed, *ACS Photonics*, 2014, 1, 285-292.
49. J. Sun, W. Yu, A. Usman, T. T. Isimjan, S. Dgobbo, E. Alarousu, K. Takanabe and O. F. Mohammed, *J. Phys. Chem. Lett.*, 2014, 5, 659-665.
50. F. Nifiatis, W. Su, J. E. Haley, J. E. Slagle and T. M. Cooper, *J. Phys. Chem. A*, 2011, 115, 13764-13772.
51. D. Eastwood and M. Gouterman, *J. Mol. Spectrosc.*, 1970, 35, 359-375.
52. T. Htun, *J. Fluoresc.*, 2004, 14, 217-222.
53. J. R. Lakowicz, *Principles of Fluorescence Spectroscopy, Springer, Singapore*, Third edn., 2006.
54. C. P. Ponce, R. P. Steer and M. F. Paige, *Photochem. Photobiol. Sci.*, 2013, 12, 1079-1085.
55. B. Lang, S. Mosquera-Vazquez, D. Lovy, P. Sherin, V. Markovic and E. Vauthey, *Rev. Sci. Insturment*, 2013, 84.
56. E. Vauthey, *J. Photochem. Photobiol. A: Chemistry*, 2006, 179, 1-12.
57. A. Rosspeintner, B. Lang and E. Vauthey, *Ann. Rev. Phys. Chem.*, 2013, 64, 247-271.
58. P. M. Keane and J. M. Kelly, *Photochem. Photobiol. Sci.*, 2011, 10, 1578-1586.
59. T. Kobayashi, K. D. Straub and P. M. Rentzepis, *Photochem. Photobiol.*, 1979, 29, 925-931.
60. T. Mani, D. M. Niedzwiedzki and S. A. Vinogradov, *J. Phys. Chem. A*, 2012, 116, 3598-3610.
61. Z. Ou, P. Chen and K. M. Kadish, *Dalton Trans.*, 2010, 39, 11272-11276.
62. A. Jammoul, S. Dumas, B. D' Anna and C. George, *Atmos. Chem. Phys.*, 2009, 9, 4229-4237.
63. O. S. Finikova, P. Chen, Z. Ou, K. M. Kadish and S. A. Vinogradov, *J. Photochem. Photobiol. A: Chemistry*, 2008, 198, 75-84.
64. F. J. Vergeldt, R. B. M. Koehorst, A. Vanhoek and T. J. Schaafsma, *J. Phys. Chem.*, 1995, 99, 4397-4405.
65. V. A. Galievsky, V. S. Chirvony, S. G. Kruglik, V. V. Ermolenkov, V. A. Orlovich, C. Otto, P. Mojzes and P.-Y. Turpin, *J. Phys. Chem.*, 1996, 100, 12649-12659.
66. T. Strozik, M. Wolszczak and M. Hilczer, *Rad. Phys. Chem.*, 2013, 91, 156-165.

Example 1 Supplemental Information

Estimation of Detection Limit for Iodide with Pt(II) TMPyP in Aqueous Phase $$\text{Detection Limit} = 3\sigma/\text{slope}$$
$$= 3 \times 0.025/67.54$$
$$= 1 \text{ pmol}$$

Multiple number of PL spectra (5-7) were recorded for the aqueous phase Pt(II)TMPyP alone. Sample Standard Deviation was calculated for the peak intensity value using 'Statistics on Columns' option in origin software and verified with online calculator. Sample Standard Deviation (0.025) is close to Population Standard Deviation (0.022). Standard deviation for the blank fluorophore, Pt(II)TMPyP porphyrin solution, without the addition of iodide was 0.025.

Figure 6:
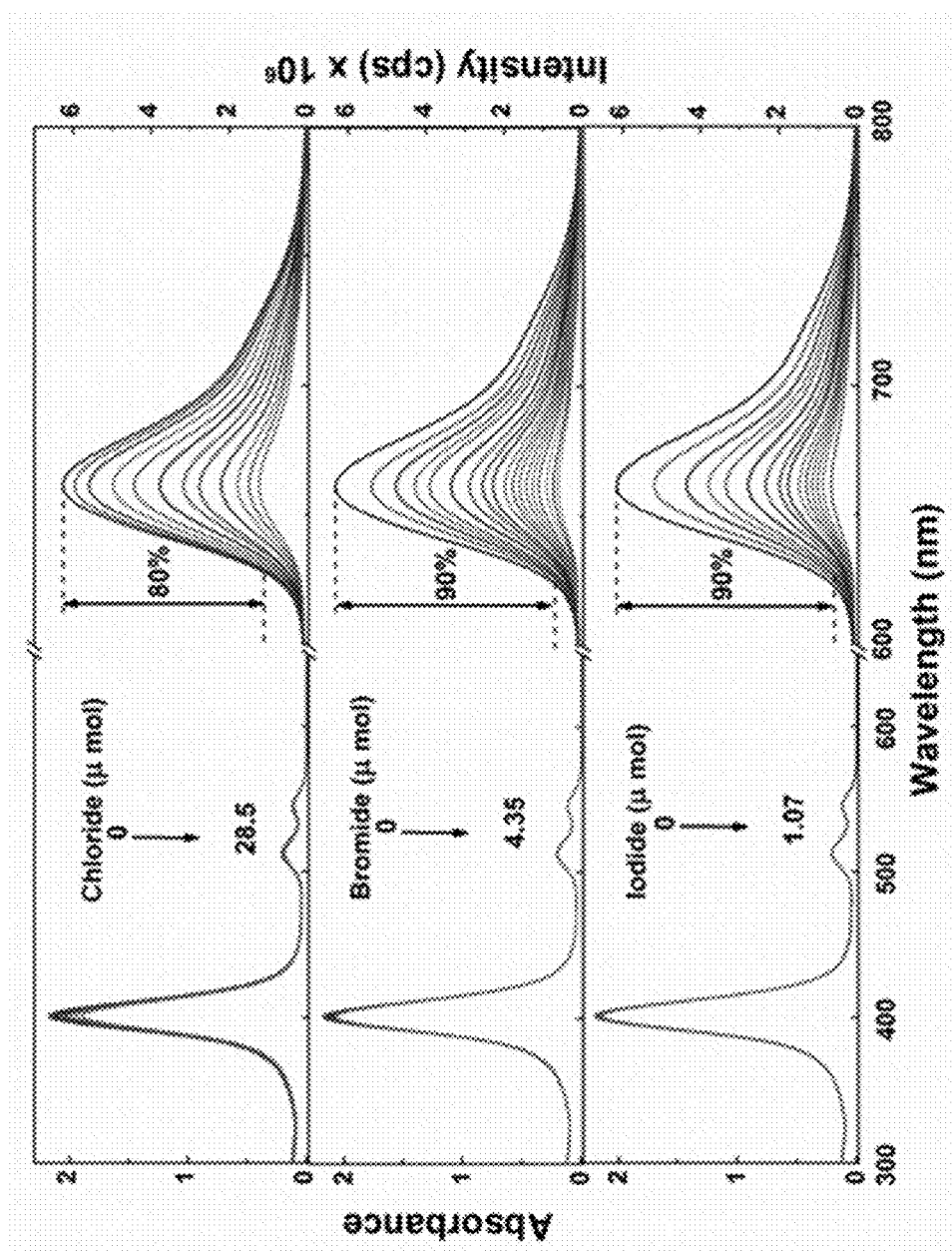
FIG. 6 demonstrates UV-Vis absorption (left), and photoluminescence (right, $\lambda_{ex}$=512 nm) spectra for Pt(II)TMPyP and after successive additions of various halides, i.e. chloride, bromide, and iodide in aqueous phase.

In the presence of halide ions, the quenching of the photoluminescence of Pt(II)TMPyP can be directly monitored upon irradiation with visible light. Pt(II) porphyrin phosphorescence was quenched to different magnitudes through the use of different halides (FIG. 1). The efficiency of quenching was experimentally demonstrated to increase in the order chloride<bromide<iodide. In the Pt(II)TMPyP porphyrin, the central cavity is filled with Pt(II) metal and that makes it interesting candidate as a sensor for the detection of halides. A previous study with metal-free porphyrin dissolved in organic solvent reported a poor sensitivity towards detection of halide (Ref. 19; Makrogeterotsikly, 2008, 50). It is interesting to note that Pt(II) porphyrin demonstrated similar sensitivity towards iodide detection in methanol (FIG. 9), and in aqueous phase (FIG. 6). A specific metal filling the central cavity of porphyrin has important role, and when Pt(II) was exchanged with Zn(II) sensing function for similarly dilute aqueous solutions of halides was almost lost (FIG. 10). It would mean that the Pt metal center is the key component of the sensing down to such an extremely detection limit.

Figure 7:
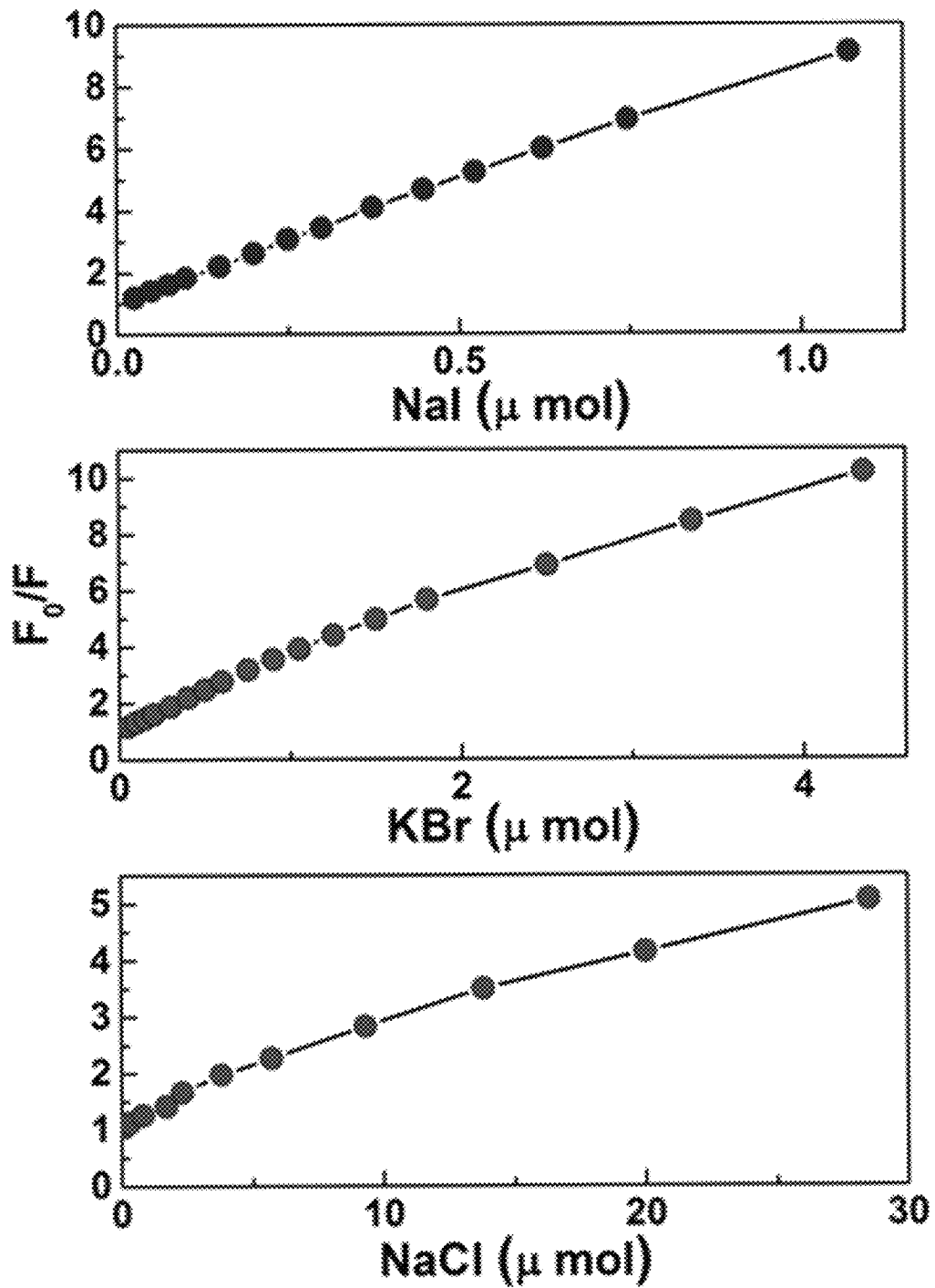
FIG. 7 shows Stern-Volmer plots for Pt(II)TMPyP, and with the maximum amounts of halides added into it for similar quenching (corresponding to PL spectra in FIG. 6).
Figure 8:
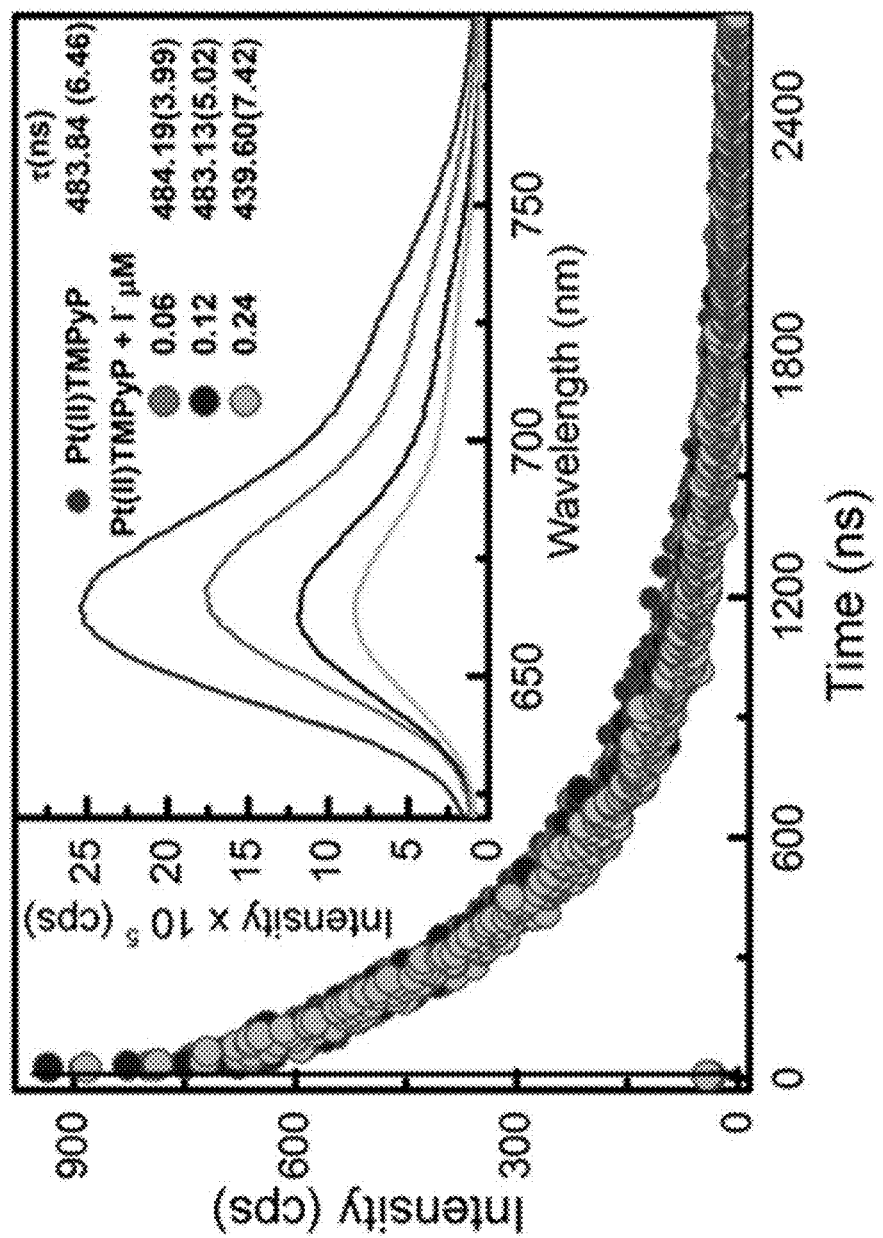
FIG. 8 illustrates time correlated single photon counting for Pt(II)TMPyP porphyrin, and with successive additions of iodide in aqueous phase. Corresponding lifetimes extracted from kinetic traces monitored at $\mu_{em}$=660 nm are given on graph and standard errors included in parenthesis.
Figure 9:
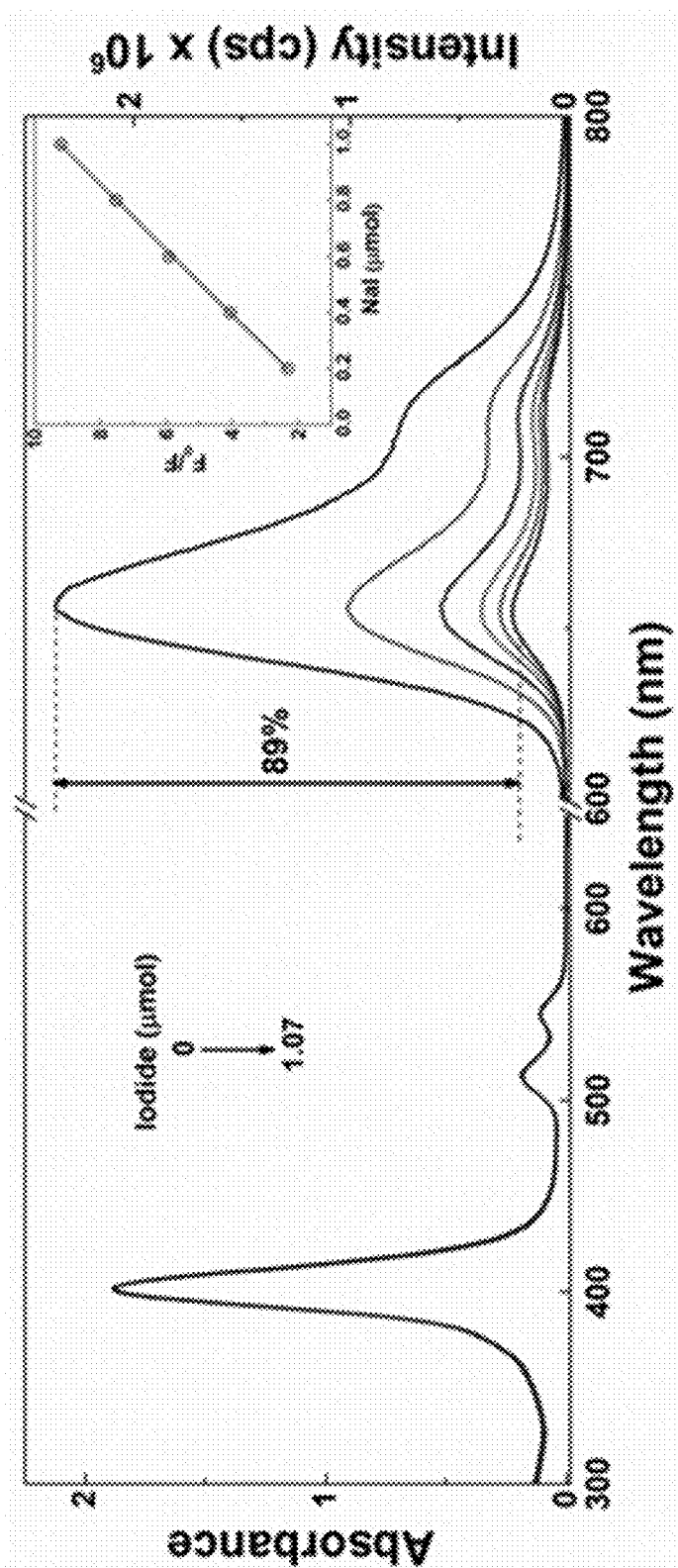
FIG. 9 shows UV-Vis absorption (left), and photoluminescence (right, $\lambda_{ex}$=512 nm) spectra for Pt(II)TMPyP, and after successive additions of iodide in organic phase, methanol.

The photoluminescence quenching upon the addition of halides indicates the presence of a photoinduced electron transfer event between the halide donor and the Pt(II) TMPyP acceptor. Non-linear Stern-Volmer plots for all of the detected halide ions indicate a static reaction for the quenching process (FIG. 7). Furthermore, the bimolecular quenching rate constant, $k_q \approx 7.8 \times 10^{12} \text{ M}^{-1}\text{s}^{-1}$ far exceeds the diffusion-controlled limit ($\sim 3 \times 10^{10} \text{ M}^{-1}\text{s}^{-1}$) establishing the fact that the quenching is due to static interaction, and confirmed by recording phosphorescence lifetimes (FIG. 8).

Figure 3:
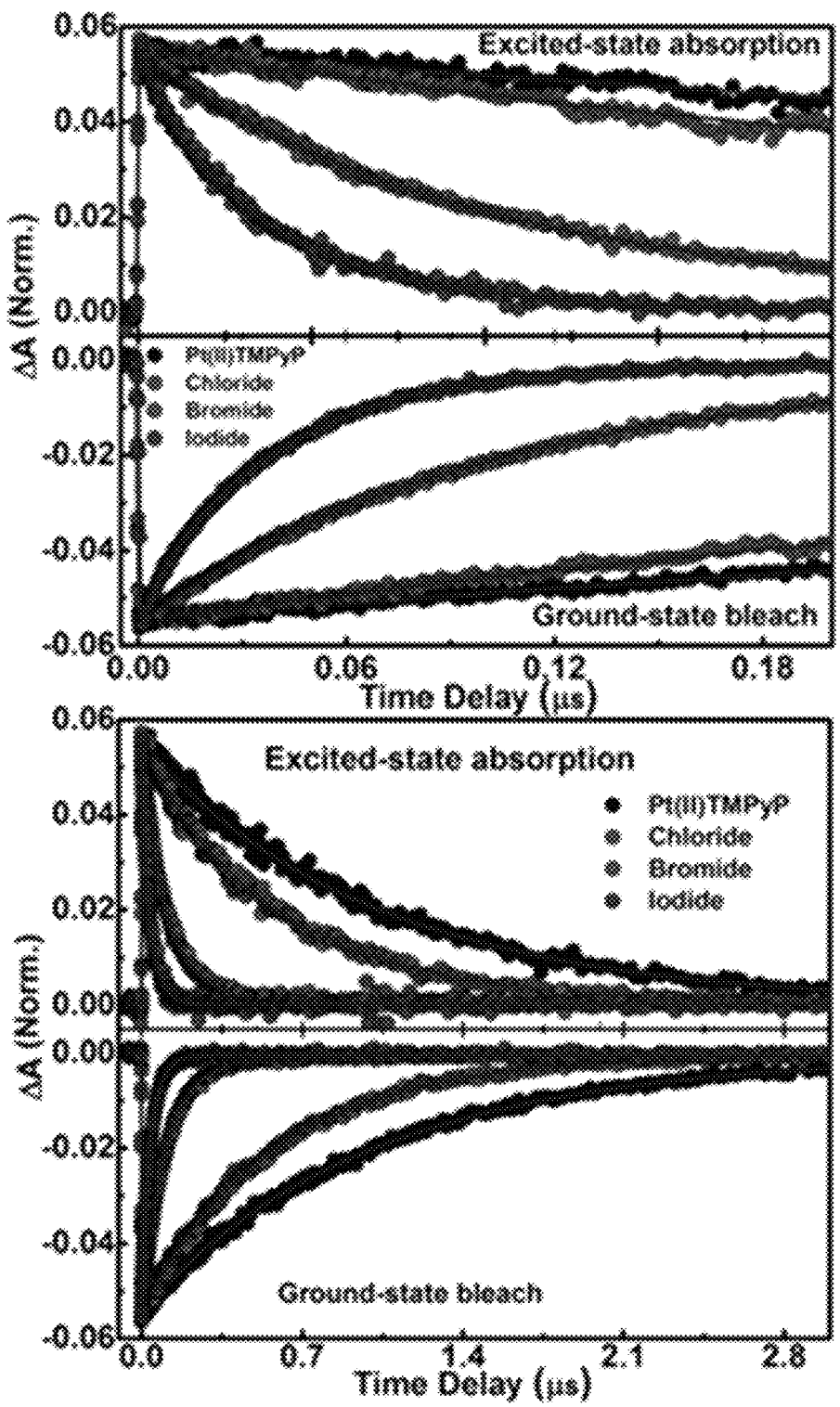
FIG. 3 shows kinetic traces of Pt(II)TMPyP with and without the successive addition of chloride, bromide and iodide in the aqueous phase. Monitoring wavelengths are 443 nm for excited-state absorption and 401 nm for ground-state bleach.

The transient absorption spectra of Pt(II)TMPyP-halides demonstrate shortening in the order; Pt(II)TMPyP alone>chloride>bromide>iodide (FIG. 2). And this was confirmed from the kinetic traces for the ground-state bleach recovery time values extracted from the transient absorption spectra (FIG. 3). This overall fast deactivation of the triplet signal implies the presence of an extra process involved in deactivation of the excited state when halides are present compared to the case of free Pt(II) porphyrin. Moreover, for the control experiment with Zn(II)TMPyP-iodide system, no appreciable changes were observed in transient absorption spectra and corresponding kinetics making a confirmation that the interaction occurs only with the Pt(II) at the macrocycle center of the porphyrin (FIG. 11A-B).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim at least the following:

1. A method of detecting anions, comprising:
    contacting a solution including an anion with a Pt(II) porphyrin;
    irradiating the solution with visible light;
    measuring a photoluminescence signal from the Pt(II) porphyrin; and
    determining the presence of the anion;
    wherein the Pt(II) porphyrin is 5, 10, 15, 20-tetra(1-methyl-4-pyridino)-porphyrin Pt(II) tetrachloride.

2. The method of claim 1, wherein the anion is selected from the group consisting of: a halogen anion, a sulfide anion, and a cyanide anion.

3. The method of claim 1, wherein the anion is iodide.

4. The method of claim 3, wherein the anion is present at a level of at least about 30 pmol in the solution.

5. The method of claim 1, further comprising: measuring a UV-Vis signal.

6. A sensor system, comprising:
    a structure having a Pt(II) porphyrin disposed on the surface;
    a compartment including a solution including an anion, wherein the anion is selected from the group consisting of a halogen anion, a sulfide anion, and a cyanide anion, wherein the anion and Pt(II) porphyrin interact to quench the photoluminescence of the Pt(II) porphyrin once the structure is placed in the compartment with the solution;
    a system for irradiating the solution with visible light; and
    a system for measuring a signal selected from a photoluminescence signal, UV-Vis signal, or a combination thereof, wherein a change in the signal relative to a signal without the anion present is correlated to the concentration of the anion in the solution.

7. The system of claim 6, wherein the anion is present at a level of at least about 30 pmol in the solution.

8. The system of claim 6, wherein the Pt(II) porphyrin is 5, 10, 15, 20-tetra(1-methyl-4-pyridino)-porphyrin (Pt(II) tetrachloride.

9. A method comprising, comprising:
    placing a structure having a Pt(II) porphyrin disposed on the surface in a compartment including a solution including an anion, wherein the anion is selected from the group consisting of a halogen anion, a sulfide anion, and a cyanide anion, wherein the anion and Pt(II) porphyrin interact to quench the photoluminescence of the Pt(II) porphyrin;
    irradiating the solution with visible light; and
    measuring a signal selected from a photoluminescence signal, UV-Vis signal, or a combination thereof, wherein a change in the signal relative to a signal without the anion present is correlated to the concentration of the anion in the solution.

10. The method of claim 9, wherein the anion is present at a level of at least about 30 pmol in the solution.

11. The method of claim 10, wherein the Pt(II) porphyrin is 5, 10, 15, 20-tetra(1-methyl-4-pyridino)-porphyrin (Pt(II) tetrachloride.

* * * * *